(12) United States Patent
Winston et al.

(10) Patent No.: US 6,752,800 B1
(45) Date of Patent: Jun. 22, 2004

(54) CATHETER HANDLE FOR CONTROLLING THE ADVANCEMENT OF A GUIDE WIRE

(75) Inventors: Thomas R. Winston, Kansas City, MO (US); John M. Neet, Lawrence, KS (US); Jeffery White, Trabuco Canyon, CA (US); John Wardle, San Clemente, CA (US); Diego D. Cueto, Laguna Niguel, CA (US)

(73) Assignee: Intraluminal Therapeutics Inc., Carlsbad, CA (US)

( * ) Notice: Subject to any disclaimer, the term of this patent is extended or adjusted under 35 U.S.C. 154(b) by 0 days.

(21) Appl. No.: 09/507,519

(22) Filed: Feb. 18, 2000

(51) Int. Cl.$^7$ .............................................. A61M 25/01
(52) U.S. Cl. ....................................... 604/528; 604/157
(58) Field of Search ........................... 604/22, 126, 435, 604/528, 95.04, 194, 157, 164.04, 164.13, 170.01, 167; 606/108; 623/1.11, 1.13

(56) References Cited

U.S. PATENT DOCUMENTS

| | | | | |
|---|---|---|---|---|
| 5,108,375 A | * | 4/1992 | Harrison et al. | 604/167.01 |
| 5,334,187 A | * | 8/1994 | Fischell et al. | 604/194 |
| 5,358,478 A | * | 10/1994 | Thompson et al. | 604/95.04 |
| 5,382,238 A | * | 1/1995 | Abrahamson et al. | 604/170.01 |
| 5,395,328 A | * | 3/1995 | Ockuly et al. | 604/528 |
| 5,397,304 A | * | 3/1995 | Trucai | 604/528 |
| 5,397,310 A | * | 3/1995 | Chu et al. | 604/158 |
| 5,415,177 A | * | 5/1995 | Zadini et al. | 600/585 |
| 5,423,331 A | * | 6/1995 | Wysham | 600/585 |
| 5,431,639 A | * | 7/1995 | Shaw | 604/264 |
| 5,456,664 A | * | 10/1995 | Heinzelman et al. | 604/528 |
| 5,599,324 A | * | 2/1997 | McAlister et al. | 604/523 |
| 5,665,072 A | * | 9/1997 | Yoon | 604/164.12 |
| 5,797,842 A | * | 8/1998 | Pumares et al. | 604/435 |
| 6,007,531 A | * | 12/1999 | Snoke et al. | 606/15 |
| 6,055,457 A | * | 4/2000 | Bonner | 607/126 |
| 6,102,887 A | * | 8/2000 | Altman | 604/22 |
| 6,146,415 A | * | 11/2000 | Fitz | 623/1.11 |
| 6,190,393 B1 | * | 2/2001 | Bevier et al. | 606/108 |
| 6,197,001 B1 | * | 3/2001 | Wilson et al. | 604/157 |
| 6,248,100 B1 | * | 6/2001 | de Toledo et al. | 604/540 |
| 6,287,330 B1 | * | 9/2001 | Johansson et al. | 623/1.13 |
| 6,626,868 B1 | * | 9/2003 | Prestidge et al. | 604/158 |
| 2001/0027323 A1 | * | 10/2001 | Sullivan, III et al. | 606/108 |

* cited by examiner

Primary Examiner—Ehud Gartenberg
Assistant Examiner—L Fastovsky
(74) Attorney, Agent, or Firm—Armstrong Teasdale LLP

(57) ABSTRACT

A catheter handle for controlling the advancement of a guide wire through a catheter is described. The catheter handle has a distal end to which is coupled a luer lock element, and a proximal end to which a control knob is coupled. The luer lock element is adaptable to allow coupling of the catheter handle to any commonly available commercial catheter. The control knob is coupled to a guide wire advancement mechanism. Movement of the control knob is translated by the advancement mechanism to advancement or braking of the guide wire.

7 Claims, 4 Drawing Sheets

CATHETER HANDLE FOR CONTROLLING THE ADVANCEMENT OF A GUIDE WIRE

BACKGROUND OF THE INVENTION

This invention relates generally to medical instruments and, more particularly, to a catheter handle for controlling the advancement of a guide wire through a body or a portion of the body, such as a blood vessel.

Guide wires are used during various interventional medical procedures to navigate therapeutic devices to a treatment site within a body, such as within a blood vessel. For example, to use a PTCA balloon device to clear an obstruction from a coronary artery, a guide wire is inserted into the femoral artery and advanced through the aorta to the obstruction in the coronary artery. The PTCA balloon device is then introduced over the wire and guided by the guide wire to the obstruction, where the balloon is then used to clear the obstruction.

However, advancing and steering guide wires through blood vessels is a difficult and risky procedure, even when practiced by skilled operators. Vessels are often tortuous or obstructed, or the tip of the guide wire itself is difficult to control. Thus, the use of guide wires typically entails the risk of puncturing or damaging the blood vessel, or else the guide wire simply fails because it is not rigid enough to penetrate certain barriers such as arterial plaque. A total occlusion of a blood vessel is an especially challenging barrier to successful use of a guide wire. Often, such occlusions are hardened by calcification and thus especially difficult to penetrate with a guide wire. When the tip of a guide wire is forced against such a hardened occlusion, the tip may be deflected toward the blood vessel wall, and, if advanced, may perforate the wall. To avoid such an undesirable outcome, the guide wire must be manually advanced by a skilled operator in carefully controlled increments. However, this is a difficult skill to acquire and even the most highly skilled operators risk damaging vessel walls. In addition, some calcified lesions present impenetrable barriers to the guide wire, even when operated by the most highly skilled operators.

Known guide wires include wires which range in diameter from 0.010 inches to 0.050 inches, and range in length from 2 feet to 10 feet. The distal tip of a typical known guide wire is shapeable into a curved or bent configuration and steered by turning the wire at the proximal end, thus transmitting torque through the wire to the distal tip. Known wires have varying degrees of rigidity (stiffness) which are selected according to the requirements of the particular procedure being performed. Softer, floppier wires are less likely to perforate vessel walls and are therefore better for navigating through tortuous arteries, but softer wires do not readily penetrate and cross occlusions. Stiffer wires are better for penetrating occlusions, but carry a greater risk of perforating or damaging vessel walls. Thus, an operator must trade off stiffness against a higher risk of perforation.

Other known guiding devices include catheters having a lumen for accommodating the movement of a guide wire. Such catheters are usually used in combination with a therapeutic device such as a PTCA balloon catheter. Known catheters also include exchange catheters, such as the Buchbinder catheter, which hold a position in the body while a wire extending through the catheter lumen is removed and replaced with a different wire. However, such catheters do not provide incremental control of guide wire advancement to minimize risk of damage.

It would therefore be desirable to provide a catheter handle for controlling the advancement of a guide wire through a catheter. It would also be desirable to provide such a catheter handle that reversibly couples with the catheter, so that the catheter handle can be removed from the catheter and coupled to another catheter. It would be further desirable to provide such a catheter handle that is adaptable for coupling with many types of catheters. It would be still further desirable to provide such a catheter handle with a braking mechanism for preventing undesired advancement of the guide wire.

BRIEF SUMMARY OF THE INVENTION

These and other objects are attained by a catheter handle for controlling the advancement of a guide wire through a catheter. In an exemplary embodiment, the catheter handle has a proximal end and a distal end, and includes an advancement mechanism for controlling the advancement of a guide wire. The distal end of the catheter handle has a luer lock fitting so that the catheter handle is reversibly attachable to most known catheters. The proximal end of the catheter handle includes a retractable control knob coupled to the advancement mechanism for manual operation of the advancement mechanism.

In one embodiment, the catheter handle includes a housing having a distal end and a proximal end. A rotating flush port is coupled to the housing distal end, and a luer lock element, for example a female luer lock element, is coupled to the flush port. At the housing proximal end, the control knob is coupled to the guide wire advancement mechanism. More specifically, the control knob is slidably engaged with a control cylinder or sleeve within the handle housing. The advancement mechanism is positioned within the control cylinder or sleeve, and includes a spring assembly. The spring assembly is configured to reversibly apply friction to the guide wire.

The spring assembly includes a spring assembly block having an opening therethrough, and a guide wire guiding channel therethrough. The guide wire guiding channel and spring assembly block opening are continuous with one another. A friction wheel engages the opening through the spring assembly block. Thus, a guide wire passing through the guide wire guiding channel makes contact with the friction wheel.

At least one geared drive wheel is coupled to the friction wheel and is rotatably coupled to the spring assembly block. In one embodiment, the geared drive wheel includes a first geared drive wheel and a second geared drive wheel of the same diameter. A first spring element is coupled to a proximal wall of the control cylinder and bows outwardly to reversibly contact the control knob. A first ratchet element is coupled to the first spring element and reversibly engages a tooth on the geared drive wheel. A second spring element extends from the control cylinder proximal wall and contacts the spring assembly block. Opposite the contact of the second spring element with the spring assembly block, the spring assembly block includes an angled pedestal. The angled pedestal reversibly engages an indentation or groove on the inner surface of the control knob. A second ratchet element extends from the control cylinder proximal wall and reversibly engages a tooth on the geared drive wheel.

In use, the control knob has a first braking position in which the spring assembly holds friction wheel in contact with the guide wire and prevents movement of the guide wire. To advance the guide wire forward in precise incremental steps, manual pressure is briefly applied to the control knob by "clicking" the knob toward the handle housing, against the force produced by the first spring element, and then releasing the control knob. The brief pressure against the first spring element causes the first ratchet element to push against the engaged tooth of the first geared wheel and to slide behind the next. A brief counterclockwise rotation of the friction wheel results. The guide wire thus is briefly urged forward. The second ratchet element in engagement with the geared drive wheel acts as a locking element against further, undesired rotation of the friction wheel. The amount of rotation of the friction wheel and thus the corresponding forward motion of the guide wire is limited by the time it takes for first ratchet element and the second ratchet element to engage the next tooth on the geared drive wheel. Thus, the guide wire is moved forward in incremental steps controlled by the engagement of the geared drive wheel by the ratchet elements.

Since the geared drive wheel has a larger diameter than the friction wheel, the actual forward movement of the guide wire is reduced by the ratio of the friction wheel diameter to the drive wheel diameter, relative to the actual forward movement of knob. The incremental rotation of the geared drive wheel, and hence the incremental advancement of the guide wire, is adjustable by altering the diameter ratio of the friction wheel to the geared drive wheel, or by altering the number of teeth on the drive wheel. In one embodiment the incremental steps are about 0.5 mm.

DETAILED DESCRIPTION OF THE INVENTION

Figure 1:
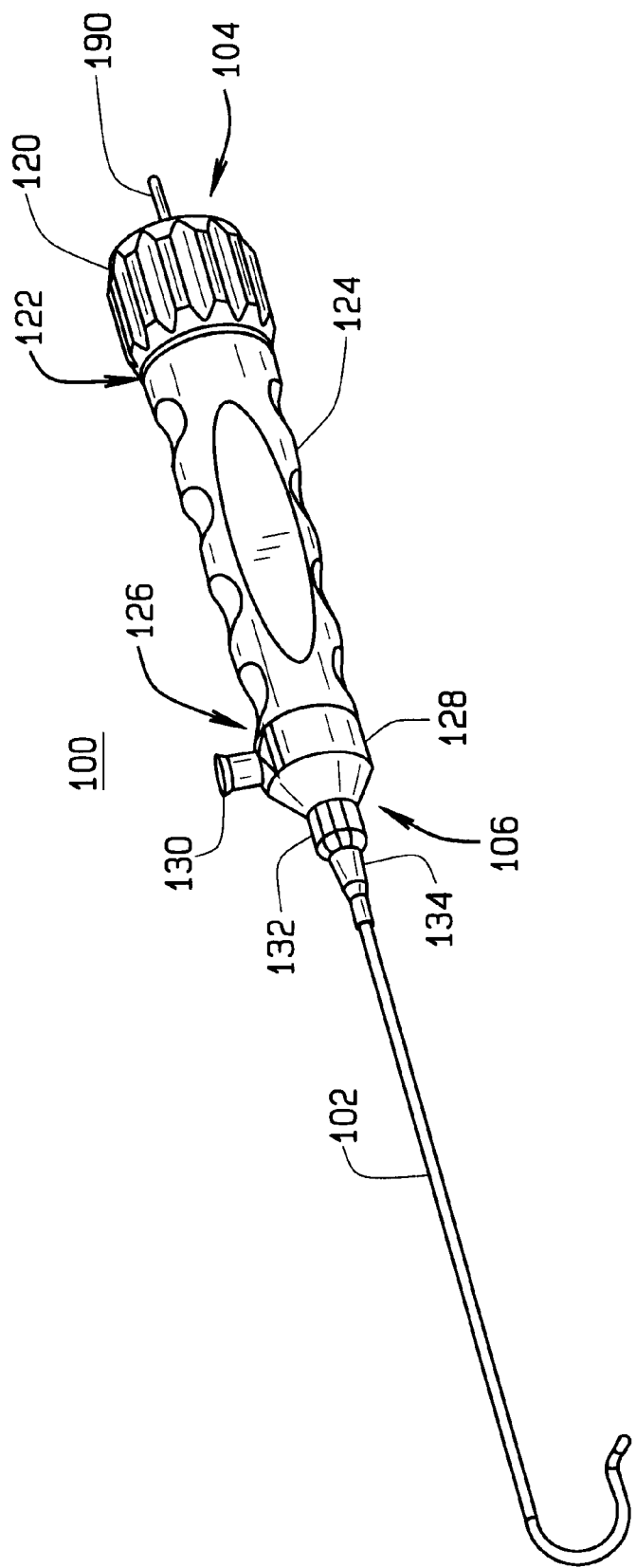
FIG. 1 is a perspective view of a catheter handle for controlling the advancement of a guide wire.

FIG. 1 is a perspective view of a catheter handle 100 for controlling the advancement of a guide wire (not shown) through a catheter. Catheter handle 100 has a proximal end 104 and a distal end 106. In an exemplary embodiment, the guide wire is introduced at catheter handle proximal end 104, passed through catheter handle 100, and into catheter 102. Catheter handle 100 includes an advancement mechanism as described in detail below. The advancement mechanism controls advancement of the guide wire through distal end 106 of catheter 102 by incrementally advancing the guide wire in precisely controlled steps.

Generally, catheter 102 is any commonly commercially available catheter fabricated from extruded thermal plastic tubing and having a central lumen (not shown) extending therethrough. The central lumen accommodates the guide wire or another device These catheters perform various functions such as supporting the guide wire, acting as a transfer catheter or as an infusion catheter, or delivering a therapeutic application such as a PTCA balloon catheter.

More specifically, handle 100 includes a control knob 120 or thumb wheel coupled to a first, proximal end 122 of a housing 124. Coupled to a distal end 126 of housing 124 is a rotating flush port 128, which includes a port connector such as a luer lock element 130 for coupling handle 100 to, for example, a syringe with saline fluid to flush the catheter and remove entrapped air. Coupled to flush port 128 is a female luer lock element 132. Female luer lock element 132 is bonded to port 128 with, for example, epoxy or another type of adhesive. Alternatively, female luer lock element 132 includes a threaded portion that is threadedly engaged with a correspondingly threaded portion of port 128. The commercial catheters that are used for catheter 102 include a male luer lock element 134 coupled to the catheter tubing. Male luer lock element 134 mates with female luer lock element 132 on catheter handle 100.

Figure 2:
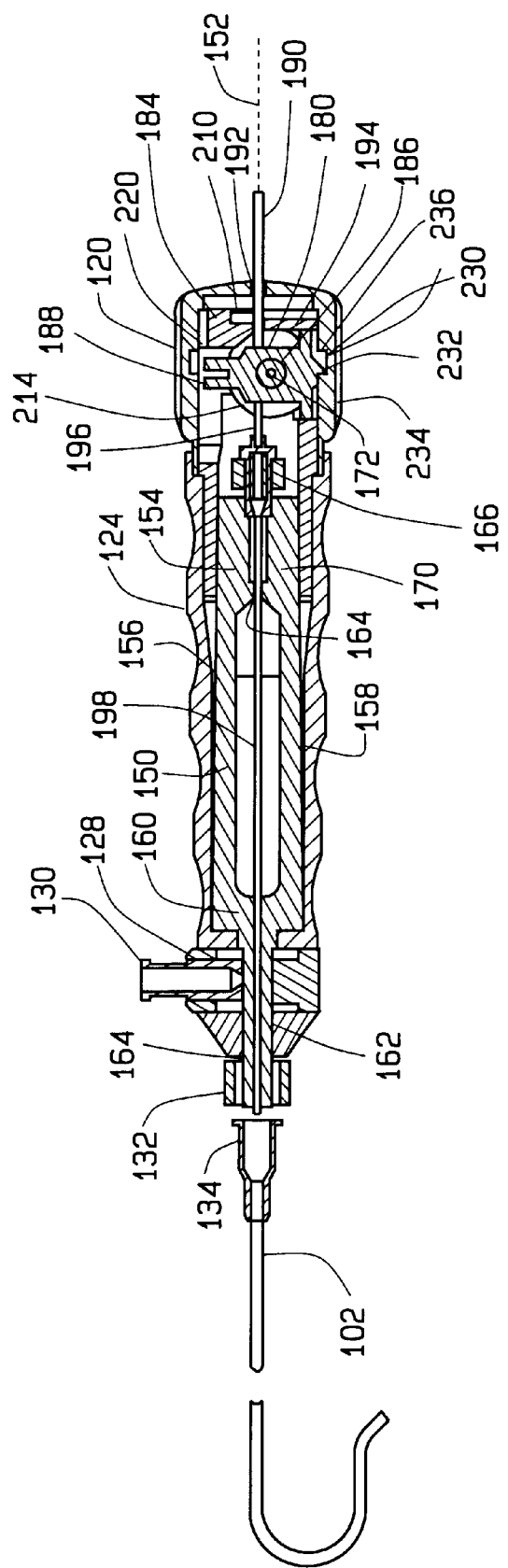
FIG. 2 is a side cross-sectional view of the catheter handle.

FIG. 2 is a side cross-sectional view of catheter handle 100. A chassis 150 extends through housing 124 and generally defines a first, long axis 152 extending the length of handle 100 from control knob 120 to female luer lock element 132. Chassis 150 is, for example, fabricated as a unitary piece from a molded plastic material. Chassis 150 includes a first, cylindrical portion 154, and a first elongate member 156 and a second elongate member 158 extending therefrom. A cross member 160 joins first and second elongate members 156 and 158, and a distal tip portion 162 is joined to cross member 160. An opening 164 extends through distal tip portion 162 and cross member 160, along long axis 152. Distal tip portion 162 extends out of housing 124, through an opening through flush port 128 and through male luer lock element 132. Cylindrical portion 154 of chassis 150 has a central bore 164 therethrough, the bore extending through cylindrical portion 154 along long axis 152. A valve assembly 166 is coupled to cylindrical portion 154 and extends therefrom.

Cylindrical portion 154 inserts into a central bore of a control cylinder 170. Control cylinder 170 is a generally cylindrical sleeve that houses an advancement mechanism 172 and slidably engages control knob 120. In an exemplary embodiment, a locking pin 174 extends from chassis cylindrical portion 154 and inserts through an opening (not shown) through control cylinder 170 to couple control cylinder 170 and chassis 168 to one another. In alternate embodiments, other means such as screws, or threading of cylinder portion 154 and control cylinder 170 are used for coupling cylinder portion 154 and control cylinder 170.

Advancement mechanism 172 controls the advancement of a guide wire inserted through handle 100, by advancing the guide wire in precisely controlled increments. Advancement mechanism 172 generally includes a spring assembly that is coupled to control knob 120 and is operable by manually pushing or "clicking" on control knob 120. More specifically, the spring assembly includes a friction wheel 180 coupled to a geared drive wheel 182. Geared drive wheel 182 is rotatably coupled to a spring assembly block 184. Spring assembly block 184 has a central opening 186 therethrough, and a guide wire guiding channel 188 extending therethrough. Central opening 186 and channel 188 are continuous. Friction wheel 180 fits within central opening 186. A first portion 190 of hypodermic tubing extends through a central opening 192 through control knob 120, through an opening (not shown) in a proximal wall 194 of control cylinder 170, and terminates where friction wheel 180 engages central opening 186 of spring assembly block 184.

A second portion 196 of hypodermic tubing extends along long axis 152 from spring assembly central opening 186, and into valve assembly 166. A third portion of hypodermic tubing 198 extends along long axis 152 from valve assembly 166, and through central bore 164 of cylindrical portion 154. Third portion 198 of tubing further extends along long axis 152 between first elongate member 156 of chassis 150 and second elongate member 158 of chassis of 150, passing through opening 164 through cross member 160 and distal tip portion 162, and terminating flush with a distal end 200 of male luer lock element 132. Thus, a guide wire inserted through first portion 190 of hypodermic tubing, and passed through channel 188 to second portion 196 of hypodermic tubing, makes contact with friction wheel 180.

Figure 3:
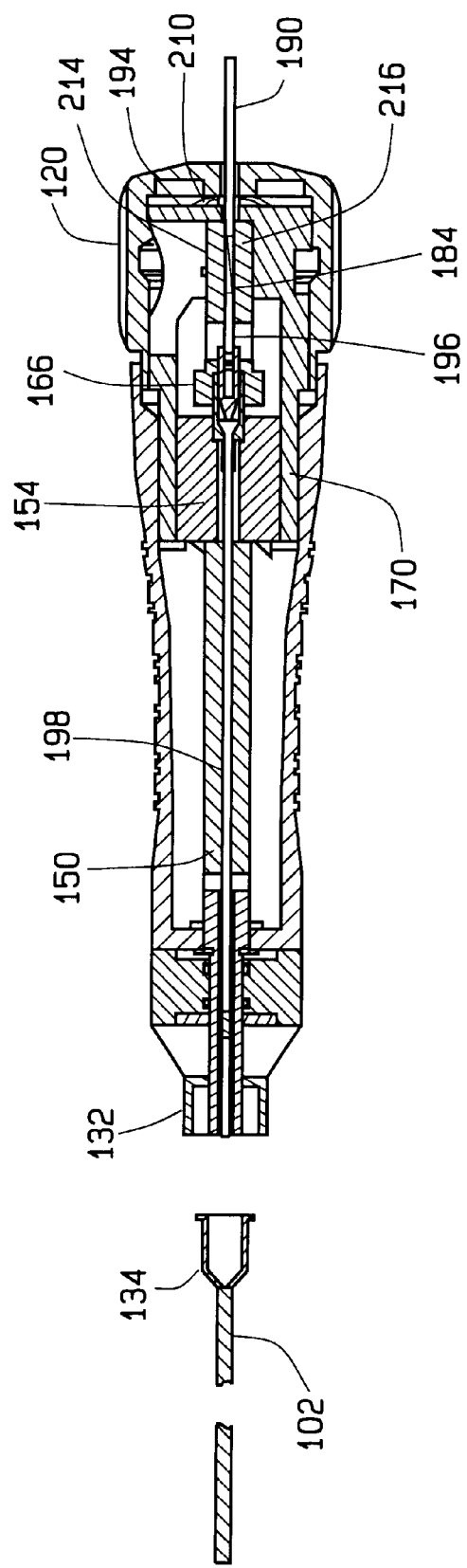
FIG. 3 is a top cross-sectional view of the catheter handle.

FIG. 3 shows a top cross-sectional view of catheter handle 100. A first, substantially C-shaped spring element 210 bows outwardly from proximal wall 194 of control cylinder 170. A first ratchet element 212 (shown in FIG. 4) is coupled to first spring element 210, and extends into control cylinder 170 to reversibly engage a tooth of geared drive wheel 182. A second ratchet element (not shown) is anchored to proximal wall 194 of control cylinder 170 and also extends into control cylinder 170 to slidably engage a tooth of drive wheel 182. In an alternative embodiment as shown in FIG. 3, geared drive wheel 182 is a pair of coupled geared wheels 214 and 216, of identical diameter, wherein spring assembly block 184 is positioned between the paired geared wheels. First ratchet element 212 engages first geared wheel 214, and the second ratchet element engages second geared wheel 216.

Referring again to FIG. 2, a second spring element 220 is anchored to proximal wall 194 above spring assembly block 184, contacting spring assembly block 184 to produce a force against spring assembly block 184. Second spring element 220 thus maintains spring assembly block 184 in a first, braking position as shown in FIG. 2. In the first position, spring assembly block 184 holds friction wheel 180 in contact with the guide wire extending through spring assembly block 184, thus impeding the forward movement of the guide wire through guiding channel 188, and locking the guide wire in place.

Figure 4:
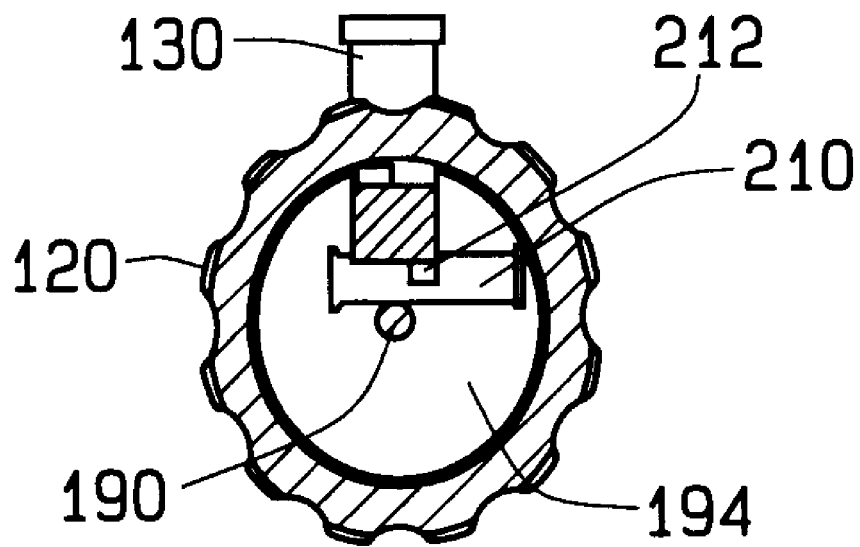
FIG. 4 is a sectional view through the proximal end of the catheter handle.

FIG. 4 is a sectional view through control knob 120, showing first spring element 210 and first ratchet element 212. In an exemplary embodiment, first ratchet element 212 is a substantially L-shaped metal strip. A first leg of first ratchet element 212 hooks over first spring element 210, while the second leg of ratchet element 210 extends into control cylinder 170. Thus, back and forth movement of spring element 210, towards and away from control cylinder proximal wall 194, causes the second leg of first ratchet element 212 to reversibly engage first geared drive wheel 214 as described above.

Opposite the contact of second spring element 220 with spring assembly block 184, spring assembly block 184 includes an angled pedestal 230 in sliding engagement with an inner surface of control knob 120. More specifically, the control knob inner surface defines a depression or indentation 232 with a first distal ramp 234 and a second proximal ramp 236. Pedestal 230 slidably engages indentation 232 so that when control knob 120 is pushed inward toward control cylinder proximal wall 194, pedestal 230 slides up proximal ramp 236, thus forcing spring assembly block 184 against second spring element 220 to a second position. In the second position, spring assembly block 184 maintains the guide wire in channel 188 away and out of contact with friction wheel 180. Once the guide wire is free of contact with friction wheel 180, the guide wire is free to move forward. The guide wire can then be advanced forward manually, free of friction wheel 180.

To advance the guide wire forward in precise incremental steps of less than about 0.5 mm, manual pressure is briefly applied to knob 120 by "clicking" knob 120 toward housing 124, against the force produced by first spring element 210, and then releasing knob 120. The brief pressure against first spring element 210 causes first ratchet element 212 to push against the engaged tooth of first geared wheel 262, and to slide behind the next tooth on the wheel. A brief counterclockwise rotation of friction wheel 180 results. The second ratchet element in engagement with second geared drive wheel 216 acts as a locking element against further, undesired rotation of friction wheel 180. The amount of counterclockwise rotation of friction wheel 180 and thus the corresponding forward motion of the guide wire is thus limited by the time it takes for first ratchet element 212 and the second ratchet element to engage the next tooth on, respectively, first and second geared wheels 214 and 216. Thus, the guide wire is moved forward in incremental steps controlled by the engagement of geared drive wheel 182, or pair of geared drive wheels 214 and 216, by the ratchet elements.

Further, since geared drive wheel 182, or pair of geared drive wheels 214 and 216, have a larger diameter than friction wheel 180, the actual forward movement of the guide wire is reduced by the ratio of the friction wheel diameter to the drive wheel diameter, relative to the actual forward movement of knob 120. The amount of advancement per each incremental advancement of the geared drive wheels is adjustable by altering the diameter ratio of friction wheel 180 to drive wheel 182 (or to pair of geared drive wheels 214 and 216), or by altering the number of teeth on the drive wheel or wheels. For example, using such alterations in alternative embodiments, incremental steps ranging up to several milimeters are achieved.

To retract the guide wire, or to move the wire freely in either direction, the operator withdraws or pulls control knob 120 from a first, "detent" or braking position in which the guide wire is held in place as described above, into a second position, away from handle housing 138, thus relieving pressure on friction wheel 180 and freeing the guide wire. To lock control knob 120 into the second position, control knob 120 has a groove (not shown) that pedestal 230 engages when control knob 120 is withdrawn. At times, it is advantageous to move the wire in a reciprocating motion to facilitate advancement through difficult tissue, such as a calcified plaque. The reciprocating motion is achieved by introducing movement in control knob 120 as described below. Control knob 120 is moved back and forth at increments of about one half the required full step movement so that the wire moves back and forth between advancing steps. This movement is accomplished, for example, with an electromagnetic actuator, a PZT crystal, or a rotating cam. Similarly, in an alternative embodiment, larger reciprocating motion is introduced by imparting reciprocating movement to spring assembly block 184, thus moving assembly block 184 and the guide wire in combination.

In an alternative embodiment of guide wire advancement mechanism 172, a roller bearing is included within or adjacent to the spring assembly, in contact with the guide wire extending through guiding channel 188, so that the guide wire moves between friction wheel 180 and the roller bearing. The roller bearing produces a force opposing the force applied to the guide wire by friction wheel 180 when spring assembly block 184 is in the first, braking position. The roller bearing acts to concentrate the frictional force from friction wheel 180 on the guide wire itself, and not on the opposing surface in spring assembly block 184, thus improving the transmission of frictional force to the guide wire.

In use, catheter handle 100 enhances the ability of a medical interventionalist to control the advancement of a variety of guide wires and to advance a guide wire past difficult tissue such as a total occlusion in a blood vessel. For example, catheter 102 is coupled to handle 100 by fitting male luer lock element 134 to female luer lock element 132. The guide wire is then loaded by feeding through proximal end 104 of catheter handle 100 and advancing through handle 100 into catheter 102. Alternatively, the guide wire is reverse fed through distal end 106 of catheter 102, and passed through handle 100 from handle distal end 108 to the handle proximal end. The proximal end of the guide wire extends past the handle proximal end 104. The guide wire and catheter in combination are introduced into the body through an introducer sheath or guiding catheter, which are both commonly commercially available. A guide wire usually has some type of bend in its distal end to facilitate steering. The operator rotates the proximal end of the wire to align the bend of the guide wire to the direction in which advancement should occur. The operator then manually advances the guide wire through the vessel.

During some procedures, such as trying to recanalize a total occlusion in an artery, the guide wire reaches the barrier of the occlusion. At this point the operator uses guide wire advancement mechanism 172 to advance the guide wire very cautiously in incremental steps, trying to penetrate the occlusion to reach the lumen of the vessel on the other side without perforating the normal artery wall. The second ratchet element engages second geared drive wheel 216 to "lock" advancement mechanism 172 and grip the guide wire. When advancement is desired, the ratcheting action of advancement mechanism 172 converts the "clicking" forward movement of control knob 120 to rotate geared drive wheels 214 and 216 forward by one tooth to the next incremental step. The second ratchet element and second geared drive wheel 216 reset to lock or hold first geared drive wheel 214 in place, while spring block assembly 184 is reset to the first, braking position by second spring element 220. The counterclockwise, "forward" movement of geared drive wheels 214 and 216 rotates friction wheel 180 to transfer the movement to the guide wire in an incremental step. The ratio of geared drive wheels 214 and 216 to friction wheel 180 serves as a transmission device to translate manual movement of the wire into incrementally advancing steps, and also to increase the forward force on the wire.

The catheter handle is suitable for use with a variety of catheter types because the luer lock coupling is adaptable to a variety of catheter diameters and types. Thus, after the catheter handle is used in combination with a disposable type catheter, the catheter is removed and discarded, while the catheter handle is reattached to a new catheter and reused. The new catheter is a new one of the same type, or alternatively is a different type of catheter or catheter device.

While the invention has been described in terms of various specific embodiments, those skilled in the art will recognize that the invention can be practiced with modification within the spirit and scope of the claims.

What is claimed is:

1. A catheter handle comprising:

a handle housing having a proximal end and a distal end;

a luer lock element coupled to said housing distal end, said luer lock element adapted for coupling with a catheter; and a guide wire incremental advancement mechanism configured for precise advancement within said handle housing, wherein the guide wire incremental advancement mechanism comprises a spring assembly, wherein said spring assembly is configured to reversibly apply friction to the guide wire and wherein said spring assembly comprises a spring assembly block having a guide wire guiding channel therethrough, wherein the guide wire extends through the guide wire guiding channel;

a friction wheel positioned to contact the guide wire; and at least one geared drive wheel coupled to said friction wheel and rotatably coupled to said spring assembly block.

2. A catheter handle in accordance with claim 1, wherein said at least one geared drive wheel comprises a first geared drive wheel and a second geared drive wheel, said first and second geared drive wheels having the same diameter.

3. A catheter handle in accordance with claim 1 wherein said guide wire advancement mechanism further comprises:

a control cylinder having a proximal wall, said control knob in sliding engagement with said control cylinder;

a first spring element coupled to said proximal wall and positioned to reversibly contact said control knob; and a first ratchet element coupled to said first spring element and in reversible engagement with said at least one geared drive wheel.

4. A catheter handle in accordance with claim 3 wherein said guide wire advancement mechanism further comprises:

a second spring element extending from said proximal wall and contacting said spring block assembly;

a second ratchet element extending from said proximal wall and in reversible engagement with said at least one geared drive wheel.

5. A catheter handle in accordance with claim 4 wherein said at least one geared drive wheel comprises a first and a second geared drive wheel and wherein said first ratchet element reversibly engages said first geared drive wheel and said second ratchet element reversibly engages said second geared drive wheel.

6. A catheter handle in accordance with claim 4 wherein said guide wire advancement mechanism further comprises a roller bearing, said roller bearing positioned to contact the guide wire, said roller bearing further positioned so that the guide wire moves between said roller bearing and said friction wheel.

7. Apparatus for controlling the advancement of a guide wire through a catheter, said apparatus comprising:

a handle for coupling to the catheter, said handle having a distal end and a proximal end, a first luer lock element coupled to said handle distal end, said luer lock element adapted for coupling to a second luer lock element on the catheter;

a handle housing, said housing enclosing a guide wire incremental advancement mechanism configured for precise advancement and a control knob coupled to said guide wire incremental advancement mechanism wherein said guide wire advancement mechanism comprises:

a spring assembly block having a guide wire guiding channel therethrough, wherein the guide wire extends through the guide wire guiding channel;

a friction wheel positioned to contact the guide wire; and at least one geared drive wheel coupled to said friction wheel and rotatable coupled to said spring assembly block wherein said guide wire advancement mechanism further comprises:

a control cylinder having a proximal wall, said control knob in sliding engagement with said control cylinder;

a first spring element coupled to said proximal wall and positioned to reversibly contact said control knob; and a first ratchet element coupled to said first sprint element and in reversible engagement with said at least one geared drive wheel.

* * * * *